United States Patent [19]
Roberts et al.

[11] Patent Number: 5,977,010
[45] Date of Patent: *Nov. 2, 1999

[54] SHAPED HYDROGENATION CATALYST AND PROCESSES FOR THEIR PREPARATION AND USE

[75] Inventors: Brian D. Roberts, South Euclid; William J. Carrick, Munson; Deepak S. Thakur, Solon, all of Ohio

[73] Assignee: Engelhard Corporation, Iselin, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 08/490,874

[22] Filed: Jun. 15, 1995

[51] Int. Cl.$^6$ ............. B01J 21/08; B01J 23/72; B01J 23/74

[52] U.S. Cl. .......... 502/244; 502/253; 502/260; 502/331; 502/338; 502/343; 502/345; 502/245; 502/259

[58] Field of Search .............. 502/345, 325, 502/329, 331, 337, 338, 343, 324, 232, 241, 244, 253, 260, 245, 259

[56] References Cited

U.S. PATENT DOCUMENTS

| | | | |
|---|---|---|---|
| 3,100,234 | 8/1963 | Lee | 260/669 |
| 3,779,946 | 12/1973 | Dorn et al. | 252/448 |
| 3,989,756 | 11/1976 | Fujise et al. | 260/580 |
| 4,188,365 | 2/1980 | Yoshioka et al. | 423/239 |
| 4,283,581 | 8/1981 | Wilkes | 568/864 |
| 4,666,879 | 5/1987 | Kelly et al. | 502/244 |
| 4,762,817 | 8/1988 | Logsdon et al. | 502/329 |
| 4,929,777 | 5/1990 | Irick et al. | 568/864 |
| 5,008,235 | 4/1991 | Wegman et al. | 502/342 |
| 5,043,509 | 8/1991 | Imai et al. | 585/466 |
| 5,093,534 | 3/1992 | Ludwig et al. | 568/881 |
| 5,124,295 | 6/1992 | Nebesh et al. | 502/64 |
| 5,134,108 | 7/1992 | Thakur et al. | 502/318 |
| 5,155,086 | 10/1992 | Thakur et al. | 502/342 |
| 5,243,095 | 9/1993 | Roberts et al. | 568/864 |
| 5,345,005 | 9/1994 | Thakur et al. | 568/885 |
| 5,418,201 | 5/1995 | Roberts et al. | 502/245 |
| 5,591,873 | 1/1997 | Bankmann et al. | 549/503 |

FOREIGN PATENT DOCUMENTS

| | | |
|---|---|---|
| A0352878 | 1/1990 | European Pat. Off. . |
| A0470344 | 2/1992 | European Pat. Off. . |
| A0522669 | 1/1993 | European Pat. Off. . |
| A888775 | 2/1962 | United Kingdom . |

*Primary Examiner*—Steven Bos
*Assistant Examiner*—Alexander G. Ghyka

[57] ABSTRACT

Shaped catalyst compositions are disclosed comprising (i) at least one metal selected from the group consisting of copper, manganese, zinc, nickel, cobalt and iron, (ii) calcium silicate and (iii) at least one clay material. Also disclosed are a process for preparing the foregoing shaped compositions and a process for hydrogenating aldehydes, ketone, carboxylic acids, carboxylic acid esters and nitro aroniate compounds using these shaped catalysts.

27 Claims, No Drawings

SHAPED HYDROGENATION CATALYST AND PROCESSES FOR THEIR PREPARATION AND USE

BACKGROUND OF THE INVENTION

1. Field of the Invention

This invention relates to catalysts which are useful as hydrogenation catalysts and particularly for the catalytic hydrogenation of aldehydes, ketones, carboxylic acids, carboxylic acid esters and nitroaromatic compounds. This invention also relates to processes for preparing said catalysts and to hydrogenation processes using said catalysts.

2. Description of Related Art

Hydrogenation reactions and catalysts useful in such reactions are well known. For example, U.S. Pat. No. 4,666,879 describes an extruded copper chromite-alumina catalyst prepared by blending together from 40–82% by weight of copper chromite and 18–60% of an extrudable alumina, typically having a pseudoboehmite or a hydroxy boehmite structure. The extruded catalyst after calcining is useful for the liquid and vapor phase hydrogenation and hydrogenolysis of various carbonyl compounds and the functional side groups of aromatic compounds. The extruded catalyst is characterized as having a surface area of between 20 and 225 square meters per gram and a packed apparent bulk density of between about 0.70 and about 1.20 g/cc.

U.S. Pat. No. 4,762,817 describes an aldehyde hydrogenation catalyst consisting essentially of a mixture of copper and zinc oxide impregnated with a minor selectivity improving amount of a selectivity enhancer comprising the combination of an alkali metal selectivity enhancer selected from the group consisting of sodium, potassium, lithium, cesium, and mixtures thereof and a transition metal selectivity enhancer selected from the group consisting of nickel, cobalt, and mixtures thereof.

U.S. Pat. No. 4,929,771 describes catalyst compositions comprised of chemically-mixed, copper-titanium oxides and the use of such catalyst compositions in the hydrogenation of certain esters to obtain the alcohol corresponding to the acid residue of the ester.

U.S. Pat. No. 5,008,235 describes a process for hydrogenating feeds into their corresponding alcohols by contact with a coprecipitated catalyst comprising copper, aluminum, and a metal (X) selected from the group consisting of magnesium, zinc, titanium, zirconium, tin, nickel, cobalt and mixtures thereof; that has been reduced with an increasing temperature during the reduction.

U.S. Pat. No. 5,043,509 describes catalyst particles employed in reactions involving the conversion of organic compounds that should possess a desired configuration in order to maintain a desired voidage which will permit passage of the feedstock through the catalyst bed during the conversion reaction. Solid phosphoric acid catalysts which comprise an admixture of an acid of phosphorus and a solid binder such as a siliceous material may be formed into polylobular, tubular, ridged, fluted, or channeled cylindrical particles which will permit a sufficient amount of voidage in the catalyst bed to be maintained even though the catalyst particles will swell during the reaction due to the formation of coke on the surface thereof.

U.S. Pat. No. 5,093,534 describes a process for the preparation of saturated alcohols from aldehydes. The hydrogenation of saturated and unsaturated aldehydes to alcohols can be carried out over catalysts containing copper and nickel. In this process, the selectivity of the alcohol preparation is further improved by a combination of an alkaline copper catalyst and a nickel-containing catalyst whose carrier material has acidic centers of a certain acid strength $H_o$.

U.S. Pat. No. 5,124,295 describes to a formed copper chromite catalyst prepared from a blend comprising from about 20 to about 80% by weight of copper chromite and from about 20 to about 80% by weight of at least one extrudable inorganic binder material wherein the catalyst has a surface area of from about 20 to about 225 $m^2/g$, and the total pore volume of the pores in said catalyst having a diameter of up to about 95,000 A is between about 0.35 to about 1 cc/g. In another embodiment, the patent describes a process for preparing this formed copper chromite catalyst and the process comprises:

(A) preparing a blend comprising from about 20 to about 80% by weight of copper chromite, from about 20 to about 80% by weight of at least one extrudable inorganic binder material, from about 1 to about 10% by weight, based on the weight of the binder, of a peptizing agent, and sufficient water to form an extrudable blend;

(B) extruding the blend to form an extrudate; and (C) calcining the extrudate. This patent also describes a process for hydrogenating aldehydes, ketones, carboxylic acids and carboxylic acid esters with catalysts of the type described.

U.S. Pat. No. 5,134,108 describes a hydrogenation catalyst comprising a major amount of the oxides of a first metal selected from copper or zinc, a second metal selected from chromium, molybdenum, tungsten and vanadium, and optionally, a minor amount of the oxide of a promoter metal selected from the group consisting of manganese, barium, zinc, nickel, cobalt, cadmium, iron and any combination thereof provided that the promotor metal is not zinc if the first metal is zinc. The average particle diameter of the powder is from about 6 to about 20 microns; and the particle surface area is from about 20 to about 70 $m_2/g$. The process for preparing this catalyst is described as comprising the steps of (A) simultaneously and separately adding to a first vessel, (1) a first aqueous solution comprising a copper zinc salt; (2) a second aqueous solution comprising a soluble base, provided that either the copper solution or the soluble base solution also contains a soluble salt of at least one second metal; or (3) a third aqueous solution comprising a soluble salt of at least one second metal is added simultaneously to the first vessel whereby an aqueous slurry of insoluble solid is formed in the first vessel, provided further that the second metal is chromium, molybdenum, tungsten, or vanadium;

(B) advancing at least a portion of the aqueous slurry from the first vessel to a second vessel;

(C) recovering the solids from the aqueous slurry in the second vessel; and (D) calcining the recovered solids.

U.S. Pat. No. 5,155,086 describes a catalyst in powdered form comprising the oxides of copper, iron, aluminum and manganese wherein the atomic ratio of copper to iron is at least 1:1 and a process for preparing such hydrogenation catalysts which comprises the steps of (A) preparing a first aqueous solution containing at least one water-soluble copper salt, at least one water-soluble iron salt, and at least one water-soluble manganese salt;

(B) preparing a second solution containing at least one water-soluble basic aluminum salt and at least one alkaline precipitating agent;

(C) mixing the first and second solutions wherein an insoluble solid is formed;

(D) recovering the soluble solid; and (E) calcining the recovered solid to form the desired catalyst. Also described is a process for hydrogenating aldehydes, ketones, carboxylic acids and carboxylic acid esters.

U.S. Pat. No. 5,345,005 describes a catalyst in powdered from which comprises a major amount of the oxides of copper and zinc, and a minor amount of aluminum oxide wherein the pore volume of pores of said catalysts having a diameter between about 120 and about 1000 A is at least about 40% of the total pore volume and a process for preparing hydrogenation catalysts comprising the oxides of copper, zinc and aluminum which comprises the steps of (A) preparing a first aqueous solution containing at least one water-soluble copper salt and at least one water-soluble zinc salt;

(B) preparing a second solution containing at least one water-soluble basic aluminum salt and at least one alkaline precipitating agent;

(C) mixing the first and second solutions whereby an insoluble solid is formed;

(D) recovering the insoluble solid. Also described is a process for hydrogenating aldehydes, ketones, carboxylic acids and carboxylic acid esters with catalysts of the type described.

There is still a need, however, for shaped chromium-free hydrogenation catalysts that have high catalytic activity which are strong and acid resistant.

SUMMARY OF THE INVENTION

In one embodiment, this invention relates to shaped catalyst compositions comprising (i) at least one metal selected from the group consisting of copper, manganese, zinc, nickel, cobalt and iron; (ii) calcium silicate and (iii) at least one clay material.

In another embodiment, the invention relates to a process for preparing a shaped catalyst which comprises:

(A) preparing a paste comprising i) at least one metal oxide wherein said metal is selected from the group consisting of copper, manganese, zinc, nickel, cobalt and iron; (ii) at least one solvent; (iii) calcium silicate; and (iv) at least one clay material;

(B) forming a shaped particle from said paste; and (C) drying and calcining said shaped particle.

In still another embodiment, this invention relates to a process for hydrogenating aldehydes, ketones, carboxylic acids, carboxylic acid esters and nitroaromatic compounds which comprises contacting said materials with the above-described catalysts under catalytic hydrogenation conditions.

DESCRIPTION OF PREFERRED EMBODIMENTS

As previously stated, this invention provides shaped catalyst compositions suitable for use in hydrogenation reactions. These compositions contain (i) at least one metal selected from the group consisting of copper, nickel, manganese, zinc, cobalt and iron.

The metal present in the compositions of the invention may be present as the reduced metal or oxide forms or as precursors to the reduced metal or oxide forms such as carbonates or nitrates which can be readily converted to the reduced metal or oxide forms or mixtures of two or more of any of these. The metals useful for the purposes of this invention may be present in one or more oxidation states. This invention also contemplates mixtures of two or more of said metals. Typically, the metal will be copper.

Usually the composition of this invention has a total metal content of copper, manganese, zinc, nickel, cobalt and iron of at least about 30%; typically from about 30% up to 75% by weight; preferably from about 35 up to 65% by weight.

The composition of this invention may also contain minor amounts of one or more promoter metals such as alkali or alkaline earth metals. If present, promoter metals are typically present in amounts from about 1% by weight up to about 10% by weight of said composition; preferably 0.5% by weight up to about 5% by weight. These metals may be present in the reduced metal or oxide forms or as precursors to such forms and in one or more oxidation states as discussed above.

The compositions of this invention are usually free of chromium and barium. The compositions are also preferably free of added alumina, i.e., alumina other than that contributed by the clay incorporated in the composition as contemplated by the invention. As used herein the compositions are free of such materials if their presence is in an amount that does not materially affect the physical, chemical and catalytic characteristics of the compositions of this invention when compared to those which are completely free of such materials. Preferably, if present, such materials will be present in trace amounts, but in amounts not greater than about 0.5% by weight, more preferably not greater than 0.1% weight.

The calcium silicate component of the compositions of this invention can be from natural or synthetic sources, or preferably, is formed in situ (hereinafter "in situ") during the preparation of the shaped catalyst composition. Typically, the catalyst composition of this invention contains up to about 50% calcium silicate; usually, from about 10% up to about 40%; and preferably, from about 20% up to about 35% by weight. It is desirable that the compositions of the invention contain up to about 20% by weight calcium; typically, from about 1 up to about 18% by weight; preferably from about 2.5 up to about 18% by weight. The silicon content of said composition is typically up to about 30% by weight; typically, from about 5 up to about 30% by weight; preferably, from about 10 up to about 20% by weight.

The compositions of this invention also contain one or more clay materials.

The clays suitable for use in this invention include alumino-silicate clays such as attapulgites, sepiolites, serpentines, kaolinites, calcium montmorillonites and mixtures thereof.

Clays useful in making compositions of the instant invention include those obtained from the Meigs—Attapulgus—Quincy fullers earth districts, located in southwest Georgia and northern Florida.

For purposes herein, the term "attapulgite" is used to mean chain lattice type clay minerals, encompassing minerals and mineral groups variously referred to in the literature as "attapulgite," "palygorskite," "sepiolite," and "hormite." Typically, the clays suitable for use in the instant invention contain a major amount of attapulgite. As used herein, "major amount" shall mean and refer to a component which is present in the largest amount of any of the components present.

Those skilled in the art will be familiar with methods to determine the relative amounts of various mineral phases present in such clays.

The clays suitable for use in the practice of this invention may be undried, dried or calcined.

The free moisture content of the clays suitable for use in this invention is preferably from about 3 up to about 8 weight percent. As used herein, the "free-moisture content" is the amount of water removed from the clay by heating to constant weight at 220° F. Typically, the clay material as mined contains up to about 45% by weight free moisture content.

The clay material for use in this invention is preferably powdered and typically has particles having mesh sizes of less than about 200 mesh (U.S. Standard), preferably less than about 325. The composition of this invention may contain up to about 30% by weight of at least one clay material; typically from about 1% up to about 30% by weight; preferably from about 3 up to about 15% by weight.

Preferably the compositions of this invention are free of added alumina other than that which may be present resulting from the clays incorporated in said compositions.

Shaped catalysts compositions of this invention can be prepared by a process which comprises:

(A) preparing a paste of (i) at least one metal oxide wherein said metal is selected from the group consisting of copper, manganese, zinc, nickel, cobalt and iron; (ii) at least one solvent; (iii) calcium silicate, (iv) at least one clay material and (v) such other optional components discussed therein.

(B) forming a shaped particle from said paste; and (C) drying and calcining said shaped particle.

The metal oxides suitable for use in preparing the compositions of this invention are the oxides of copper, manganese, zinc, nickel, cobalt and iron. As used herein "metal oxides" includes the precursors of such oxides such as carbonates and nitrates.

The metal oxides used in the process of the instant invention are typically in a physical form suitable for the formation of shaped particles; preferably the metal oxides used herein are in powdered form.

The process of this invention also includes the use of one or more solvents selected from conventional liquid solvents which are inert in the context of the process of the instant invention. These solvents include, but are not limited to, water: alcohols, such as methanol, ethanol and propanol; ketones, such as acetone and methyl ethyl ketone; and aldehydes, such as propanal and butanal. In a preferred embodiment, water is used as the solvent.

The amount of solvent used in preparing the paste in the instantly claimed process is an amount that provides a consistency which allows for a shape to be formed out of said paste, but not so fluid as to fail to hold the formed shape. Typically, the total amount of solvent in the paste including that contributed by other components such as clay is from about 20 up to about 60% by weight of the paste; preferably from about 35% up to about 55% by weight of the paste.

The calcium silicate useful for the purposes of this invention may be from naturally occurring or synthetic sources. The calcium silicate may be in one or more of its several forms including calcium metasilicate ($CaSiO_3$), dicalcium silicate ($Ca_2SiO_3$) and tricalcium silicate ($Ca_3SiO_5$). The calcium silicate may be formed ex situ or in situ. Ex situ formed calcium silicate is that which is formed separate from the presence of one or more of the components used in the preparation of the shaped compositions of the instant invention. Typically this involves use of a commercially available source of calcium silicate which is mixed with the other components used in the preparation of the shaped compositions of instant invention. Calcium silicate formed in situ is that which is formed in the presence of one or more of the components used in the preparation of the shaped compositions of the invention. For the purpose of this invention, in situ calcium silicate may be formed in the presence of the source of metal or the clay material although, preferably, the calcium silicate is formed in the presence of a mixture of the source of metal and the clay material. Typically, the in situ formed calcium silicate is formed by contacting, prior to the shaping of said composition, at least one source of calcium with at least one source of reactive silica.

The source of calcium, as used herein, refers to non-halogen and non-sulfur calcium salt which are capable of reacting with a reactive silica source to form calcium silicate, such as oxides, nitrates, carbonate, etc. Suitable sources of such calcium nitrate, calcium hydroxide, calcium carbonate, etc.

The reactive source of silica, as used herein, refers to a silicon-containing material capable of reacting with the calcium source, under ambient conditions of temperature and pressure, to form calcium silicate. Suitable sources of such silica include acid or base stabilized silica sols, sodium silicate, potassium silicate, etc.

The molar ratio of calcium to silicon added to the paste is preferably about 1:1, although typically can range from 0.6:1.4 to 1.4 to 0.6. In addition, the paste typically has an atomic ratio of said metal to calcium to silicon of 2.5 to 6.0:0.6 to 1.4:0.6 to 1.4.

The paste of the instant process may also contain rheology control agents and pore forming agents. Rheology control agents include starches, sugars, glycols, polyols, powdered organic polymers, graphite, stearic acid and its esters. Pore forming agents include graphite, polypropylene or other organic polymer powders, activated carbon, charcoal, sugars, starches and cellulose flour. The rheology control agents and pore forming agents are well-known to those of ordinary skill in the art and are used as necessary to obtain the desired viscosity of the paste or porosity of the formed particle as the case may be. Typically, either one of these may be present in an amount of from about 0.5% up to about 20% by weight, preferably from about 1% up to about 10% by weight of the paste.

The metal oxide, solvent, calcium silicate (and/or source of calcium and reactive source of silica) and optional rheology control agents, pore forming agents, promoter materials and clay are mixed or mulled thoroughly for a period of time sufficient to provide uniform mixing of the components. This time can vary from a few minutes to several hours. Preferably, the mixture is mixed or mulled for a total period of from about 5 minutes to about 120 minutes, more preferably from about 10 minutes up to about 90 minutes. This is typically carried out at room temperature at or about atmospheric pressure. A formed particle is then prepared from the paste. Extrusion is the preferred forming technique and typically the formed shape is a cylinder, although other shapes such as tubular, polylobular, fluted, and ridged are also useful. The formed particle is then dried to remove the bulk of the solvent from said particle. Typically, drying is done at a temperature of from about 80° up to about 300° C. in air for a period of up to 24 hours, preferably from about 6 hours up to about 12 hours. The particle is then calcined in air or inert gas for a period of time ranging from about one hour up to about 12 hours, preferably two to eight hours at a temperature of from about 400° C. up to about 1000° C., preferably about 600° C. to about 850° C. The result is a hard, and low bulk density formed particle. In the context of this invention a particle typically has a hardness of 4–12 lbs/mm side crush strength, surface area is typically from about 5 up to about 150 m$^2$/g, preferably, 10 up to 100 m$^2$/g; and packed bulk density is typically less than 1.4 gms./cc, preferably from about 0.6 up to about 1.4 gms./cc. and more preferably from about 0.6 up to about 1.1 gms./cc. When used herein, hardness is determined by ASTM-04179-82; surface area is determined by B.E.T. N$_2$ adsorption method (ASTM-4222-83); and packed bulk density is determined by ASTM-D4164-82.

Following calcination, but before use, the catalyst may be and is normally activated by reducing at least some of the metal oxide present in the catalyst. The reduction step may be carried out in situ immediately prior to use, or alternatively, reduction may be carried out in advance of use by contacting the catalyst with hydrogen or a mixture of hydrogen and nitrogen at elevated temperatures according to well-known procedures in which a portion or all of the metal oxide are reduced. The reduced catalyst may then be stabilized or passivated, e.g., by exposing the catalyst to air or CO$_2$ to form a thin oxide layer on the surface, or the reduced catalyst may be stored in a protective medium such as an inert liquid until use.

The catalysts of the present invention are useful for hydrogenating aldehydes, ketones, carboxylic acids and carboxylic acid esters to alcohols and nitroaromatic compounds to amino aromatic compounds.

The shaped catalysts of this invention may be utilized in fixed bed reactors.

In one embodiment, carboxylic acids and carboxylic esters can be converted to alcohols in excellent yields. A wide variety of acids, particularly esters of carboxylic acids can be treated with the catalyst of the present invention to produce alcohols. The esters may be monoesters or diesters. Among the acids which may be hydrogenated to the corresponding alcohols without isolating the ester include stearic acids and caproic acids. Esters derived from the alcohols of lower molecular weight carboxylic acids are hydrogenated more rapidly and at lower temperatures than the esters derived from the higher alcohols. Examples of esters which may be hydrogenated with the catalyst of the present invention include the methyl ester of coconut fatty acid, methyl stearate, methyl oleate, ethyl laurate, ethyl myristate, the diethyl ester of ethyl malonic acid, diethyl succinate, di-n-butyl glutarate, diethyl sebacate. As noted, the esters are converted to alcohols, and examples of such conversions include: ethyl laurate to lauryl alcohol; ethyl myristate to myristyl alcohol; ethyl valerate to n-amyl alcohol; methyl caproate to n-hexyl alcohol, etc.

Examples of aldehydes which may be hydrogenated to alcohols with the catalyst of the present invention include: butyraldehyde, furfural, 2-ethylhexenal, dodecanal, tetradecanal, etc. Examples of ketones include acetone, acetophenone, etc.

The hydrogenation reactions which are conducted in the presence of the catalyst of the present invention are carried out at temperatures of from about 100° C. to about 350° C. and at pressures of from about 15 psi to about 4500 psi.

Examples of this invention are included herein below of course, these examples are not intended as limiting this invention as modification of the examples by ordinary expedient will be readily apparent to those of ordinary skill in the art.

Unless otherwise indicated in the following examples and elsewhere in the specification and claims, all parts and percentages are by weight, temperatures are in degrees Centigrade and pressures are at or near atmospheric.

EXAMPLE 1

A one-gallon plow-type mixer is charged with 500 parts of technical grade (76–78% Cu) cupric oxide, 137 parts of Micro-Cel E (a synthetic calcium silicate commercially available from Celite Corp., Lompoc, Calif.), and 85.3 parts Attagel 30 attapulgite clay (commercially available from Engelhard Corporation, Iselin, N.J.), and mixed for five minutes. Next, 445 parts of water is added to the mixer, while mixing, over a 19 minute period. The mixer is discharged and the resulting mass is extruded through a die plate with 0.140 inch diameter round holes and dried overnight at 125° C. The resulting extrudates are calcined in air at 560° C. for about two hours.

EXAMPLE 2

A one-gallon plow-type mixer is charged with 500 parts of technical grade cupric oxide, 219 parts of Micro-Cel E calcium silicate, and 78.2 parts Attagel 30 clay and mixed for five minutes. Next, 550 parts of water is added to the mixer, while mixing, over a 37 minute period. The mixer is discharged and the resulting mass is extruded through a die plate with 0.140 inch diameter round holes and dried overnight at 110° C. The resulting extrudates are calcined in air at 665° C. for about one hour.

EXAMPLE 3

A one-gallon plow-type mixer is charged with 1300 parts of technical grade cupric oxide, 88 parts of reagent grade calcium hydroxide, 50 parts of Zusoplast PS1 (a polysaccharide extrusion aid commercially available from Miles, Inc., Pittsburgh, Pa.), and 133 parts of Attagel 30 clay, and mixed for ten minutes. Next, 230 parts of Nalco 2327 colloidal silica (commercially available from Nalco Chemical Co., Naperville, Ill.), diluted with 100 parts of deionized water, is added while mixing, and the mixing is continued for another ten minutes. Next, a solution made up of 100 parts of deionized water and 193.6 parts of reagent grade 50% sodium hydroxide solution is added to the mixer while running. The mixing is continued for 35 minutes, during which time, a total of 70 parts of additional deionized water is added. The mixer is discharged and the resulting mass is extruded through a die plate with 0.140 inch diameter round holes. The extrusions are next fed through the extruder again and dried overnight at 125° C. The resulting extrudates are calcined in air at 525° C. for about three hours.

EXAMPLE 4

A one-gallon plow-type mixer is charged with 900 parts of technical grade cupric oxide, 122 parts Attagel 30 clay, 170 parts of reagent grade calcium hydroxide, and 5 parts of Zusoplast PS1 and mixed for ten minutes. Next, 22 parts of reagent grade 50% sodium hydroxide solution is added to 720 parts of P.Q. N-grade sodium silicate solution (commercially available from P.Q. Corp., Chester, Pa.) and diluted with 370 parts of deionized water. This solution is added to the powders, while mixing, and the mixing is continued for another twenty minutes. The mixer is discharged and the resulting mass is extruded through a die plate with 0.140 inch diameter round holes. The extrusions are dried overnight at 125° C and calcined in air at 450° C. for about one hour.

EXAMPLE 5

A one-gallon plow-type mixer is charged with 1000 parts of technical grade cupric oxide, 356.2 parts of reagent grade calcium hydroxide, 48 parts of Zusoplast PS1, and 79.8 parts Attagel 30 clay and mixed for five minutes. Next, 849.6 parts of Nalco 1034A colloidal silica is added while mixing, and the mixing is continued for another 27 minutes. Next, a total of 225 parts of water is added while mixing, over a 34 minute period. The mixer is discharged and some of the resulting mass is extruded through a die plate with 0.140 inch diameter round holes and dried overnight at 125° C. The resulting extrudates are calcined in air at 600° C. for about two hours.

EXAMPLE 6

A one-gallon plow-type mixer is charged with 1000 parts of technical grade cupric oxide, 356.2 parts of reagent grade calcium hydroxide, 48 parts of Zusoplast PS1, and 79.8 parts Attagel 30 clay and mixed for five minutes. Next, 849.6 parts of Nalco 1034A colloidal silica is added while mixing, and the mixing is continued for another 27 minutes. A total of 225 parts of water is added while mixing, over a 34 minute period. The mixer is discharged and some of the resulting mass is extruded through a die plate with 0.140 inch diameter round holes and dried overnight at 125° C. The resulting extrudates are calcined in air at 600° C. for about two hours.

EXAMPLE 7

A 40 gallon plow-type mixer is charged with 45 parts of technical grade cupric oxide, 13.5 parts of reagent grade calcium hydroxide, 3.5 parts of Zusoplast PS1, and 7.5 parts of Attagel 30 clay and mixed for a minute. Next, 32.2 parts of Nalco 1034A colloidal silica diluted with 18.5 parts water is added while mixing, and the mixing is continued for another 36 minutes. Another 8 parts of water is added during the course of the mixing. Next, the mixer is discharged and the resulting mass is extruded through a die plate with 0.140 inch diameter round holes and dried overnight at 175° F. A portion of the resulting extrudates are calcined in air at 660° C. for about two hours.

EXAMPLE 8

A 40 gallon plow-type mixer is charged with 40 parts of technical grade cupric oxide, 12 parts of reagent grade calcium hydroxide, 3.1 parts of Zusoplast PS1, and 6.7 parts of Attagel 30 clay and mixed for 3 minutes. Next, 24 parts of Nalco 2327 colloidal silica diluted with 16 parts water is added while mixing, and the mixing is continued for another 3 minutes. Next, 2.6 parts of 70% reagent grade nitric acid, diluted with 9 parts water is added while mixing. The mixing is continued for another 10 minutes. Next, the mixer is discharged and the resulting mass is extruded through a die with 5-fluted holes of 3.5 millimeter diameter and dried overnight at 175° F. The resulting extrudates are calcined in air at 680° C. for about two hours.

EXAMPLE 9

A one-gallon plow-type mixer is charged with 800 parts of technical grade cupric oxide, 187 parts of reagent grade calcium hydroxide, 6 parts of Zusoplast PS1, and 160 parts Attagel 30 clay and mixed for twenty minutes. A solution, made up of 446 parts of Nalco 1034A colloidal silica plus 892 parts of a technical grade manganese nitrate solution (15.5% Mn), is added while mixing, and the mixing is continued for another twenty minutes. The mixer is discharged and the resulting mass is extruded through a die plate with 0.140 inch diameter round holes and dried overnight at 125° C. The resulting extrudates are calcined in air at 500° C. for about two hours.

COMPARATIVE EXAMPLE A

A one-gallon plow-type mixer is charged with 800 parts of technical grade cupric oxide, and 602 parts Attagel 30 clay and mixed for five minutes. Next, 690 parts of water is added to the mixer, while mixing, over a 36 minute period. The mixer is discharged and the resulting mass is extruded through a die plate with 0.140 inch diameter round holes and dried overnight at 110° C. The resulting extrudates are calcined in air at 560° C. for about four hours.

COMPARATIVE EXAMPLE B

A one-gallon plow-type mixer is charged with 800 parts of technical grade cupric oxide, and 327 parts Attagel 30 clay and mixed for five minutes. Next, 535 parts of water is added to the mixer, while mixing, over a 9 minute period. The mixer is discharged and the resulting mass is extruded through a die plate with 0.140 inch diameter round holes and dried overnight at 110° C. The resulting extrudates are calcined in air at 560° C. for about two hours.

COMPARATIVE EXAMPLE C

A one-gallon plow-type mixer is charged with 500 parts of technical grade cupric oxide, and 337 parts of Micro-Cel E calcium silicate and mixed for five minutes. Next, 715 parts of water plus 33.5 parts of reagent grade 70% nitric acid is added to the mixer, while mixing, over a 41 minute period. Next 40 parts of Zusoplast PS1 is added and mixed for two minutes. The mixer is discharged and the resulting mass is extruded through a die plate with 0.140 inch diameter round holes and dried overnight at 125° C. The resulting extrudates are calcined in air at 585° C. for about two hours.

The hydrogenation tests, for which results are given in Tables 1–4, were carried out in test stands that consist of a catalyst activation system, an feed reservoir and pump, the reactor section, and a gas/liquid separator section for recovery of the product. The reactors are stainless steel tubes with three heating zones surrounding the catalyst bed and preheating section. Concurrent, downflow configuration was used for both gas and liquid reactants. Hydrogen and nitrogen gas for catalyst activation and reactant hydrogenation, are metered through mass flow control devices. Each catalyst is activated by controlled hydrogen reduction of the active copper oxide component before starting the reaction. A multifunctional strip chart recorder is used to collect temperature, pressure, and flow data at preselected time intervals throughout the run.

The vapor phase ethyl-propyl-acrolein (EPA) hydrogenation test reported in Table 1 employs a catalyst volume of 150 milliliters. A minimum time of 23 hours was used to equilibrate the reaction rates and achieve steady-state conditions before hydrogenated 2-ethyl-hexanal (2-EH) product was sampled for gas chromatographic analysis. Feedstock and products were analyzed for C8 aldehydes, C8 alcohols, undifferentiated light-end and heavy-end hydrocarbon byproducts. The 2-ethyl-2-hexenal feedstock was obtained from a domestic, commercial source and stored under an inert atmosphere (nitrogen) while in use. Test conditions were chosen to (a) ensure vapor phase conditions prevailed throughout the reaction zone, and (b) to enable conversion and selectivity differentiation between catalysts. The following reaction conditions were applied: inlet temperature=95° C.; inlet pressure=14.7 psig (absolute); LHSV (aldehyde)= 0.30 hrs-1; GHSV (hydrogen)=2241 hrs-1; and hydrogen/aldehyde (molar)=50.

Table 1 compares Examples 1,2, and 7 with Comparative Examples A, B and C. The Table shows that the catalysts of the invention have much better activity and selectivity for the conversion of ethyl-propyl acrolein (EPA) to 2-ethyl-hexanol (2-EH) than catalysts with similar contents of the active metal (copper). Example 7, the preferred embodiment, has better activity and selectivity than examples 1 and 2. The catalyst of example 7 also has the highest crush strength, as well. The compositions of the control examples were chosen so as to demonstrate the effects of varying levels of clay or commercial synthetic calcium silicate on the performance of the extrusions. The Table shows that using only clay or commercial synthetic calcium silicate as binders does not impart the performance seen with the use of the both together. This is an unexpected synergistic effect that is seen to an even greater degree in the catalyst of the preferred embodiment, which uses the calcium silicate formed in-situ.

The vapor phase furfural to furfuryl alcohol hydrogenation test reported in Table 2 employs a catalyst volume of 100 milliliters. The feedstock and products were analyzed forfurfural, furfuryl alcohol, furan, and undifferentiated light-end and heavy-end hydrocarbon byproducts. The furfural feedstock was obtained from a domestic, commercial source and distilled to remove as much residual sulfur-containing impurity as possible. It was stored under an inert atmosphere (nitrogen) while in use. Test conditions were chosen to (a) ensure vapor phase conditions prevailed throughout the reaction zone, and (b) to enable conversion and selectivity differentiation between catalysts, and (c) reflect current commercial usage.

TABLE 1

Vapor-Phase Ethyl-Propyl-Acrolein Hydrogenation
Test Conditions: Inlet Temperature = 95° C.; Pressure = ambient;
150 cc Catalyst Bed Volume; 24 Hours On-Stream

| Catalyst | Avg. Bed Temp. (° C.) | EPA Conversion (Wt. %) | 2-EH Selectivity (Wt. %) | Surface Area ($m^2$/gm) | Crush Strength (lbs/mm) | Packed A.B.D. (gms/cc) | % Cu (wt. %) | % Clay (wt. %) | % CaSiO3 (wt. %) (Source) |
|---|---|---|---|---|---|---|---|---|---|
| Control Example 1 | 107 | 66.1 | 48.76 | 77 | 6.4 | 0.92 | 62 | 38 | 0 |
| Control Example 2 | 115 | 87.4 | 54.90 | 59 | 5.9 | 1.04 | 75 | 25 | 0 |
| Control Example 3 | 116 | 85.8 | 47.85 | 47 | 3.6 | 0.75 | 62 | 0 | 38 (comm.*) |
| Example 1 | 125 | 92.5 | 77.55 | 48 | 4.2 | 0.97 | 72 | 10 | 18 (comm.*) |
| Example 2 | 131 | 98.9 | 86.8 | 50 | 2.2 | 0.86 | 62 | 10 | 28 (comm.*) |
| Example 7 | 134 | 99.3 | 92.00 | 33 | 7.4 | 1.09 | 61 | 8.5 | 29.5 (in situ) |

*comm.: commercially obtained calcium silicate

Table 2 gives data comparing a commercial non-chromium copper catalyst (Engelhard Cu-0320T: 61% Cu, 20% Na2SiO3) with Examples 3 and 4 of the present invention. The data show that the catalysts of the invention have activities and selectivities comparable to the commercial catalyst, but are both stronger and less dense. The lower density is very desirable in commercial operation due to the lowered cost of filling a given reactor volume (since these types of catalysts are always sold by weight). The increased crush strength means there is less likelihood of attrition during shipping and less chance of a catalyst bed collapsing during use.

The vapor phase nitrobenzene to aniline hydrogenation test reported in Table 3 employs a small catalyst volume of 25 milliliters due to the highly exothermic nature of this reaction. The feedstock and products were analyzed for nitrobenzene and aniline. The feedstock was obtained from a domestic, commercial source and the test conditions were chosen to reflect current commercial usage.

TABLE 2

FIXED BED HYDROGENATION OF FURFURAL
Catalyst Volume - 100 cc

| Catalyst | Hours On Stream | FCHO Conversion (% wt.) | FA Selectivity (% wt.) | Surface Area ($m^2/g$) | Crush Strength (lb/mm) | Packed A.B.D. (g/cc) |
|---|---|---|---|---|---|---|
| Reference Catalyst | 1–3 | 95.8 | 97.0 | 6.0 | 4.2 | 1.88 |
| (commercially available | 4–6 | 88.9 | 97.6 | | | |
| copper catalyst; 61% Cu, | 21–23 | 65.8 | 97.9 | | | |
| 20% Na2SiO3) | 24–26 | 63.4 | 97.9 | | | |
| | 26–30 | 61.2 | 97.8 | | | |
| | 45–47 | 50.9 | 97.8 | | | |
| Example 3 | 1–3 | 89.8 | 97.8 | 9.0 | 8.4 | 1.57 |
| | 4–6 | 77.5 | 98.5 | | | |
| | 21–23 | 56.2 | 98.9 | | | |
| | 24–26 | 54.1 | 98.9 | | | |
| | 27–29 | 52.1 | 98.9 | | | |
| | 45–47 | 43.5 | 98.9 | | | |
| Example 4 | 1–3 | 84.2 | 97.7 | 40 | 6.3 | 1.11 |
| | 4–6 | 73.8 | 98.3 | | | |
| | 21–23 | 55.1 | 98.7 | | | |
| | 24–26 | 53.3 | 98.8 | | | |
| | 27–29 | 51.6 | 98.7 | | | |
| | 45–47 | 42.9 | 98.7 | | | |

Table 3 compares Example 6 with a copper chromite catalyst used commercially (Engelhard Cu-1152T: 29% Cu, 26% Cr, 7% Ba, 15% $CaSiO_3$) for the hydrogenation of nitrobenzene to aniline. The nitrobenzene hydrogenation data show that the catalyst of the invention gives better activity than the commercial catalyst and does so with higher strength and much lower bulk density (offering the same advantages mentioned above).

The liquid phase C12 methylester hydrogenation test reported in Table 4 employs a catalyst volume of 200 milliliters. A minimum time of 24 hours was used to equilibrate the reaction rates and achieve steady-state conditions before hydrogenated C12 alcohol product was sampled for gas chromatographic analysis. Feedstock and products were analyzed for C8–C14 esters, C8–C14 alcohols, undifferentiated light-end and heavy-end hydrocarbon by-products.

The C12 feedstock was obtained from a domestic, commercial source and stored under an inert atmosphere (nitrogen) while in use. Test conditions were chosen to reflect current commercial usage. The bed temperature was varied from 180 to 200° C.; two inlet pressures were used: 4350 psig and 3510 psig; two LHSVs were used: 0.50 and 1.0 hrs-1; and hydrogen/ester (molar)=44–100.

Table 4 compares Examples 6 and 8 with a commercially available reference catalyst (Engelhard Cu- 1987 T1/8: 36% Cu, 33% Cr, 3% Mn). The activity of the catalysts are reported in saponification value (sap. value) which indicates the degree of remaining ester feedstock (or other saponifiable intermediates) and is reported in units of milligrams of potassium hydroxide (KOH) per grams of product. The sap. value of the feedstock is 265. The table shows that the catalysts of the invention have better activity and selectivity for the conversion of C12 methylester to C12 alcohol than a state-of-the-art commercial copper chromite catalyst. At the higher pressure (4350 psig), Example 6 gives saponification values that are about the same or slightly lower than the reference catalyst. However, the bulk density of the catalyst of the invention is about half that of the commercial copper chromite. At the lower pressure (3510 psig), Example 6 produces product with saponification values that are approximately half that of the reference for a given temperature and liquid hourly space velocity (LHSV). The hydrocarbon byproduct make is very low for all of the runs. Example 8 is nominally the same diameter and length as the reference catalyst and Example 6, but has a 5-fluted cross-sectional shape. This extrusion shape serves to lower the bulk density of the extrusions even further and also offers more external surface area for enhanced feed/product diffu-

TABLE 3

FIXED BED HYDROGENATION OF NITROBENZENE TO ANILINE
Catalyst Volume = 25 cc

| Catalyst | Hours On Stream | Avg. Bed Temp. (° C.) | N.B. Conversion (% wt.) | Surface Area ($m^2/g$) | Crush Strength (lb/mm) | Packed A.B.D. (g/cc) |
|---|---|---|---|---|---|---|
| Reference Catalyst | 14–15 | 204 | 96.3 | 70 | 3.8 | 1.5 |
| (commercial copper chromite | 17–19 | 207 | 96.5 | | | |
| 29% Cu, 26% Cr, 7% Ba, | 21–23 | 209 | 96.0 | | | |
| 15% CaSiO3) | | | | | | |
| Example 6 | 14–15 | 200 | 99.5 | 58 | 5.1 | 0.84 |
| | 17–20 | 198 | 99.6 | | | |
| | 21–23 | 199 | 99.6 | | | | sion. This catalyst gives saponification values that are about an order of magnitude lower than the reference catalyst for a given set of temperatures and LHSVs. In addition, it is possible to lower the operating pressure to 2500 psig and still obtain a low saponification value. Obviously, one could reduce the space velocity and increase the temperature to enable operation at even lower pressures with this catalyst. Thus, the preferred embodiment of the present invention, extruded in various shapes, offers the following advantages relative to current commercial catalysts: much lower coat-to-fill, greater activity, lowered operating pressure, and very good selectivity.

TABLE 4

FIXED BED HYDROGENOLYSIS OF C-12 METHYL ESTER.
Catalyst Volume = 200 cc

| Catalyst | Run No. | Sap. Value (mg KOH/gm) | Hydro-carbons (wt. %) | Bed Temp. (° C.) | LHSV V/V/Hr. | Pressure (psig) | P.A.B.D. (gms/cc) |
|---|---|---|---|---|---|---|---|
| Reference Catalyst | 7-5 | 5.9 | 0.044 | 200 | 1.0 | 4350 | 1.55 |
| (commercial copper chromite | 7-6 | 9.5 | 0.027 | 190 | 1.0 | 4350 | |
| 36% CuO, 33% Cr, 3% Mn) | 7-7 | 26 | 0.000 | 180 | 1.0 | 4350 | |
| | 7-3 | 2.1 | 0.067 | 180 | 0.5 | 4350 | |
| Example 6 | 9-6 | 5.4 | 0.026 | 200 | 1.0 | 4350 | 0.85 |
| | 9-2 | 7.0 | 0.012 | 190 | 1.0 | 4350 | |
| | 9-4 | 15 | 0.005 | 180 | 1.0 | 4350 | |
| | 9-3 | 2.5 | 0.013 | 180 | 0.5 | 4350 | |
| Reference Catalyst | 26-2 | 11.9 | 0.001 | 200 | 1.0 | 3510 | 1.55 |
| (Pressure reduced | 26-3 | 20.5 | 0.015 | 190 | 1.0 | 3510 | |
| to 3510 psig) | 26-4 | 4.1 | 0.001 | 190 | 0.5 | 3510 | |
| | 26— | — | — | 180 | 1.0 | 3510 | |
| Example 6 | 30-2 | 7.9 | 0.019 | 200 | 1.0 | 3510 | 0.85 |
| (Pressure reduced | 30-3 | 12.1 | 0.008 | 190 | 1.0 | 3510 | |
| to 3510 psig) | 30-4 | 2.7 | 0.021 | 190 | 0.5 | 3510 | |
| | 30— | — | — | 180 | 1.0 | 3510 | |
| Example 8 | 29-2 | 1.2 | 0.022 | 200 | 1.0 | 3510 | 0.67 |
| (Pressure reduced to | 29-3 | 2.0 | 0.009 | 190 | 1.0 | 3510 | |
| to 3510, 3000, & | 29-5 | 0.4 | 0.020 | 190 | 0.5 | 3510 | |
| 2500 psig) | 29-4 | 4.6 | 0.003 | 180 | 1.0 | 3510 | |
| | 29-6 | 3.7 | 0.008 | 1 90 | 1.0 | 3000 | |
| | 29-7 | 4.1 | 0.009 | 190 | 1.0 | 2500 | |

We claim:

1. A shaped catalyst composition comprising a uniform mixture of (i) at least one metal selected from the group consisting of copper, nickel, manganese, zinc, and cobalt; (ii) calcium silicate; and (iii) at least one clay material, wherein said composition is prepared by a process which comprises:

(A) preparing a paste comprising (i) at least one metal oxide wherein said metal is selected from the group consisting of copper, manganese, zinc, nickel, and cobalt; (ii) at least one solvent; (iii) calcium silicate; and (iv) at least one clay material;

(B) forming a shaped particle from said paste; and (C) drying and calcining said shaped particle.

2. A composition according to claim 1, wherein said composition is free of chromium, barium and added alumina.

3. A composition according to claim 1 wherein said composition contains up to about 30% by weight of said clay.

4. A composition according to claim 1 wherein the total metal content of copper, nickel, manganese, zinc, and cobalt in said composition is at least about 30% by weight.

5. A composition according to claim 1 wherein said composition contains up to about 20% by weight calcium.

6. A composition according to claim 1 wherein said metal is copper.

7. A composition according to claim 1 wherein said metal is present in an amount from about 30 up to about 75% by weight of said composition.

8. A composition according to claim 1 wherein said clay material is selected from the group consisting of attapulgites, sepiolites, serpentines, kaolinites, calcium montmorillonites and mixtures thereof.

9. A composition according to claim 1 wherein said calcium silicate is formed in situ.

10. A composition according to claim 1 wherein said composition contains from about 1 up to about 15% by weight calcium.

11. A composition according to claim 1 wherein said compositions has a silicon content of from about 1 up to about 30% by weight.

12. A composition according to claim 1 wherein the surface area of said composition is from about 10 up to about 100 $m^2/g$.

13. A composition according to claim 1 wherein the packed bulk density of said composition is from about 0.6 up to about 1.4 cc/g.

14. A composition according to claim 1 wherein said shape is formed by extrusion and the formed shape is circular, tubular, polylobular or fluted.

15. An extruded catalyst composition comprising a uniform mixture of (i) at least one metal oxide of copper, manganese or mixtures thereof; (ii) calcium silicate formed in situ by contacting, prior to the extrusion, calcium hydroxide and a stabilized silica sol; and (iii) at least one clay material; wherein said composition has a total copper content of from about 35 up to about 65% by weight; a calcium content of from about 2.5 up to about 18% by weight, a silicon content of from about 10 up to about 20% by weight, a surface area of from about 10 up to about 100 $m^2/g$., and a packed bulk density of from about 0.6 up to about 1.1 cc/g.

16. A process for preparing a shaped catalyst which comprises:

(A) preparing a paste comprising a uniform mixture of (i) at least one metal oxide wherein said metal is selected from the group consisting of copper, manganese, zinc, nickel, and cobalt; (ii) at least one solvent; (iii) calcium silicate; and (iv) at least one clay material;

(B) forming a shaped particle from said paste; and (C) drying and calcining said shaped particle.

17. A process according to claim 16 wherein said metal is copper.

18. A process according to claim 17 wherein said paste is free of chromium and added alumina.

19. A process according to claim 17 wherein said paste contains up to about 30% by weight of at least one clay material.

20. A composition according to claim 1 wherein said calcium silicate is formed by the in situ reaction of a source of calcium and a reactive source of silica.

21. A composition according to claim 20 wherein said source of calcium is a calcium salt.

22. A composition according to claim 21 wherein said calcium salt is selected from the group consisting of calcium oxide, calcium nitrate, calcium oxalate, calcium acetate, calcium hydroxide, calcium carbonate and mixtures thereof.

23. A composition according to claim 20 wherein said reactive source of silica is stabilized silica sol, alkali metal silica or mixtures thereof.

24. A process according to claim 16 wherein said paste has an atomic ratio of said metal to calcium to silicon is 2.5 to 6.0: 0.6 to 1.4: 0.6 to 1.4.

25. A composition prepared by the process of claim 16.

26. A process for preparing a shaped catalyst which comprises:

(A) preparing a paste comprising a uniform mixture of (i) at least one iron oxide; (ii) at least one solvent; (iii) calcium silicate; and (iv) at least one clay material;

(B) forming a shaped particle from said paste; and (C) drying and calcining said shaped particle, wherein said paste is free of chromium and added alumina and said paste has an atomic ratio of said iron to calcium to silicon is 2.5 to 6.0: 0.6 to 1.4: 0.6 to 1.4.

27. A process according to claim 26, wherein said calcium silicate is formed in situ.

* * * * *